United States Patent
Ritchie

(10) Patent No.: US 9,522,075 B1
(45) Date of Patent: Dec. 20, 2016

(54) SPORTS INJURY ABATEMENT SYSTEMS

(71) Applicant: Anthony L. Ritchie, Littleton, CO (US)

(72) Inventor: Anthony L. Ritchie, Littleton, CO (US)

( * ) Notice: Subject to any disclaimer, the term of this patent is extended or adjusted under 35 U.S.C. 154(b) by 405 days.

(21) Appl. No.: 14/098,485

(22) Filed: Dec. 5, 2013

Related U.S. Application Data

(60) Provisional application No. 61/733,843, filed on Dec. 5, 2012.

(51) Int. Cl.
*A61F 5/00* (2006.01)
*A61F 5/01* (2006.01)

(52) U.S. Cl.
CPC .................. *A61F 5/0102* (2013.01)

(58) Field of Classification Search
CPC ........ A61F 5/01; A61F 5/0102; A61F 5/0104; A61F 5/0111; A61F 5/0113; A61F 5/0195; A61F 5/0585; A61F 5/14
See application file for complete search history.

(56) References Cited

U.S. PATENT DOCUMENTS

| | | | | |
|---|---|---|---|---|
| 5,776,090 A * | 7/1998 | Bergmann | ............ | A61F 5/0111 128/882 |
| 6,447,469 B1 * | 9/2002 | Ritchie | ................. | A61F 5/0111 128/882 |
| 6,490,737 B1 * | 12/2002 | Mazzei | ................. | A61G 13/12 128/846 |
| 6,945,947 B2 * | 9/2005 | Ingimundarson | ..... | A61F 5/0113 128/882 |
| 2007/0038169 A1 * | 2/2007 | Alon | ..................... | A61F 5/0111 602/27 |
| 2012/0330206 A1 * | 12/2012 | George | ................. | A61F 5/0111 602/27 |
| 2014/0090274 A1 * | 4/2014 | Arquilla | ............... | A43B 1/0045 36/83 |

* cited by examiner

*Primary Examiner* — Kristen Matter
(74) *Attorney, Agent, or Firm* — Ramon L. Pizarro; Edwin H. Crabtree

(57) ABSTRACT

An ankle support for wearing over a person's lower leg and foot is disclosed. The ankle support includes a yoke made of a semi-rigid, flexible material. The yoke includes a shin portion and a stirrup portion. A removable cap that is adapted for extending over the stirrup portion of the yoke is used with the ankle support. The removable cap includes a groove for engaging the stirrup portion of the yoke. Additionally, a separate shin section cover that is adapted for extending over the shin portion of the yoke and include a groove that will accept a mating portion of the yoke is also provided. The shin section cover can be varied independently of the removable cap.

4 Claims, 8 Drawing Sheets

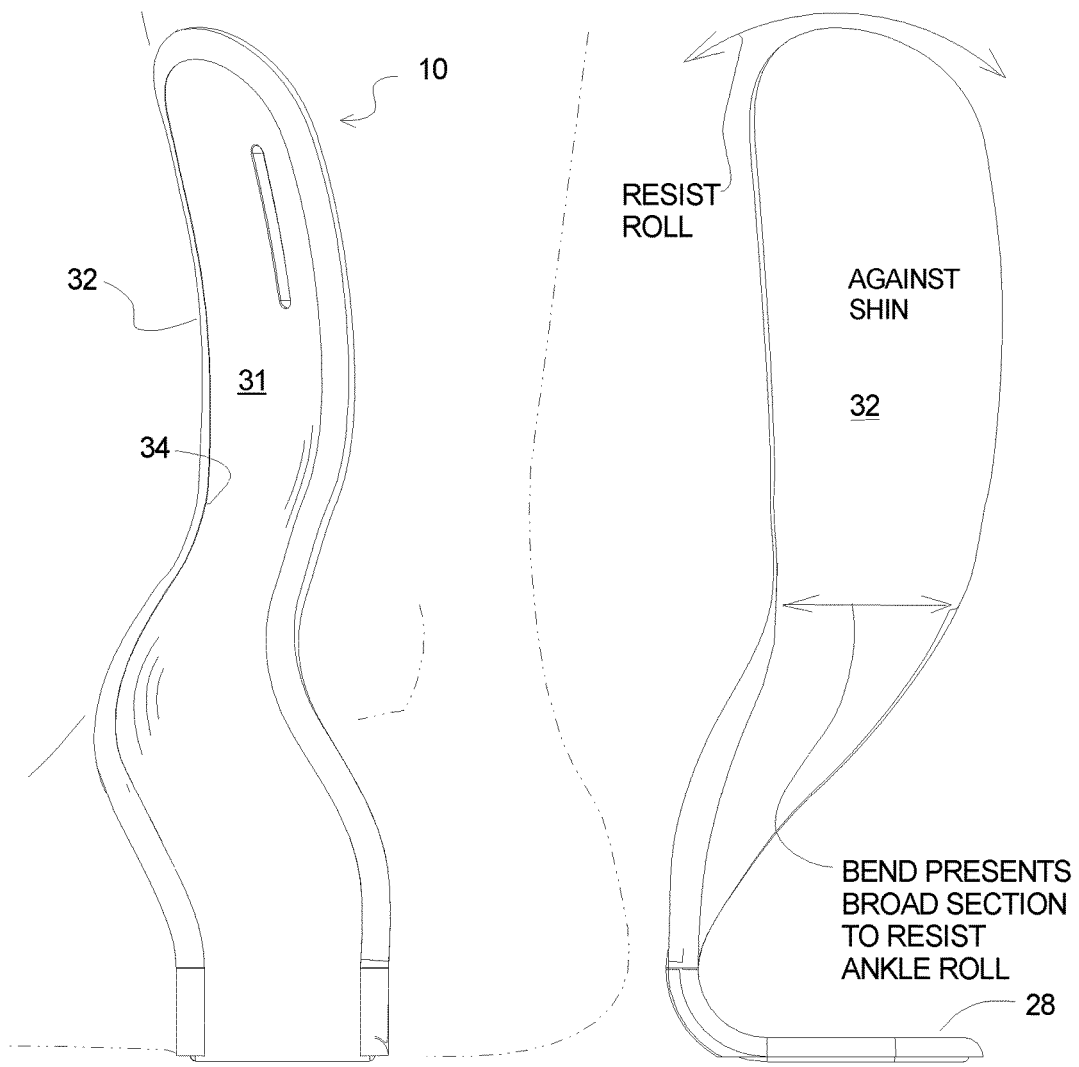
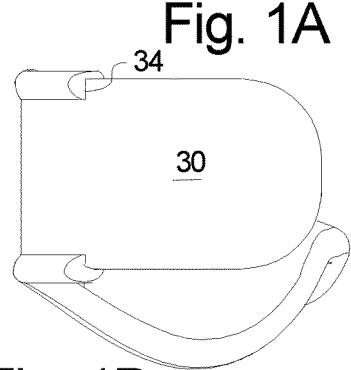
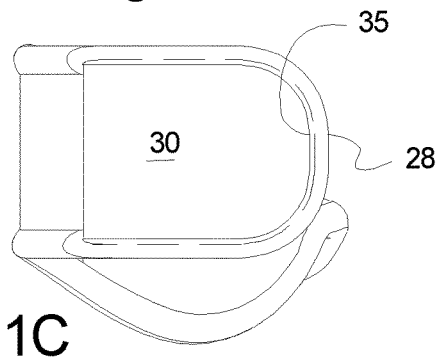
Fig. 1A  Fig. 1B  Fig. 1C  Fig. 1D

SPORTS INJURY ABATEMENT SYSTEMS

This application claims the benefit of my U.S. provisional application titled SPORTS INJURY ABATEMENT SYSTEMS, having Ser. No. 61/733,843, filed Dec. 5, 2012.

BACKGROUND OF THE INVENTION (a) Field of the Invention

This invention generally relates to a devices or system for minimizing injuries while participating in sports or other activities that may expose the human body to injuries from collisions or from movement, such as side-to-side movements while playing sports.

(b) Discussion of Known Art

The prevention of injury to ankles, as well as the treatment of injured ankles, requires the provision of pressure and support to the area around the injured ankle. There are many known devices that for this purpose. However, the amount of support provided by these devices is often compromised by the need to provide the injured individual with mobility in order to prevent the accumulation of fluids around the injured area. Thus known devices have either provided excessive structure that inhibits the mobility of the user, which in turn has detrimental effects to the recovery of the individual, or provided too little support where needed.

Examples of known devices include U.S. Pat. No. 3,867,239 to Alesi, incorporated herein by reference in its entirety, U.S. Pat. No. 5,038,762 to Hess et al., incorporated herein by reference in its entirety, U.S. Pat. No. 5,527,269 to Reithofer, U.S. Pat. No. 5,090,404 to Kallassy, U.S. Pat. No. 6,447,469 to Ritchie, incorporated herein by reference in its entirety, U.S. Pat. No. 6,093,468 to Toms et al., incorporated herein by reference in its entirety, and U.S. Pat. No. 6,447,469 to Ritchie, also incorporated herein by reference in its entirety.

SUMMARY

Injuries from participating in sports occur frequently, and can have serious and lasting effects on a person's mobility, particularly if not treated promptly and appropriately. Common injuries include sprained or twisted ankles, trauma to various parts of the body due to collisions with other sports participants or with things encountered while participating in sports. Often an important aspect of preventing long-term or permanent damage due to sports injuries is providing the appropriate first aid or support for the injured areas.

Ideally, preventing sports injuries is a preferred way to avoid the long-term effects of injuries. However, the fact that such injuries are so common is a testament to the fact that there is a need for adequate, inexpensive and readily available protective equipment.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which:

FIG. 1 is a perspective view of an embodiment of an L-shaped stirrup portion used with wrapping as shown in my U.S. Pat. No. 6,447,469, the yoke having over-molded rubberized cushioning material that ends just be before the stirrup portion (30).

Figure 2:
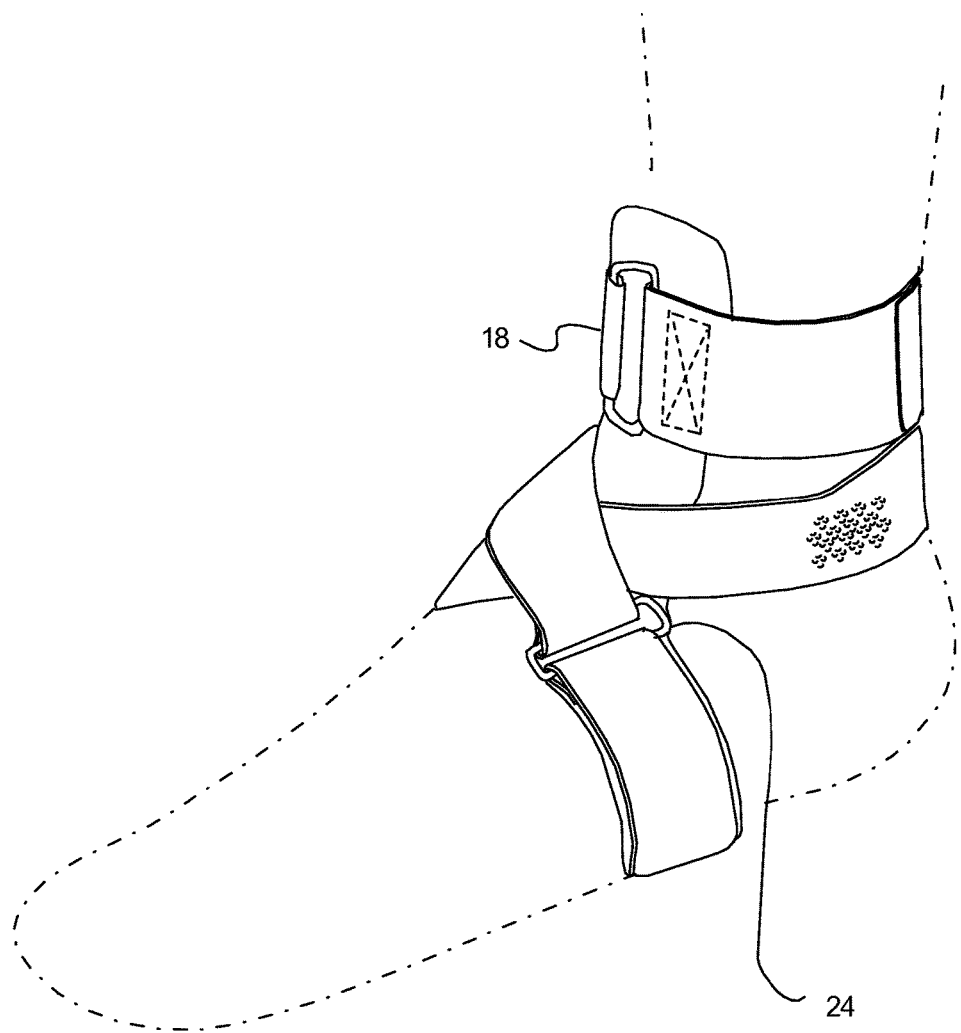
FIG. 2 illustrates the wrapping of ankle strap and the lower-calf strap, and illustrates that by producing a device without cushioning on the stirrup portion, one produces an ankle wrap that cooperates with the insert of a shoe, and thus can be worn with athletic shoes without discomfort.
Figure 3:
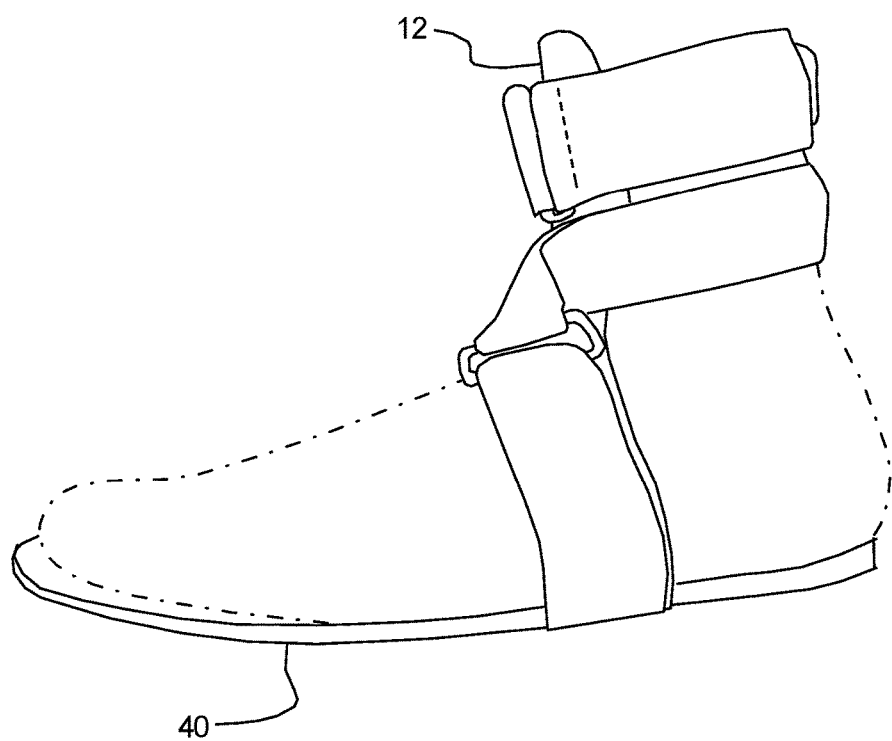
Figure 4:
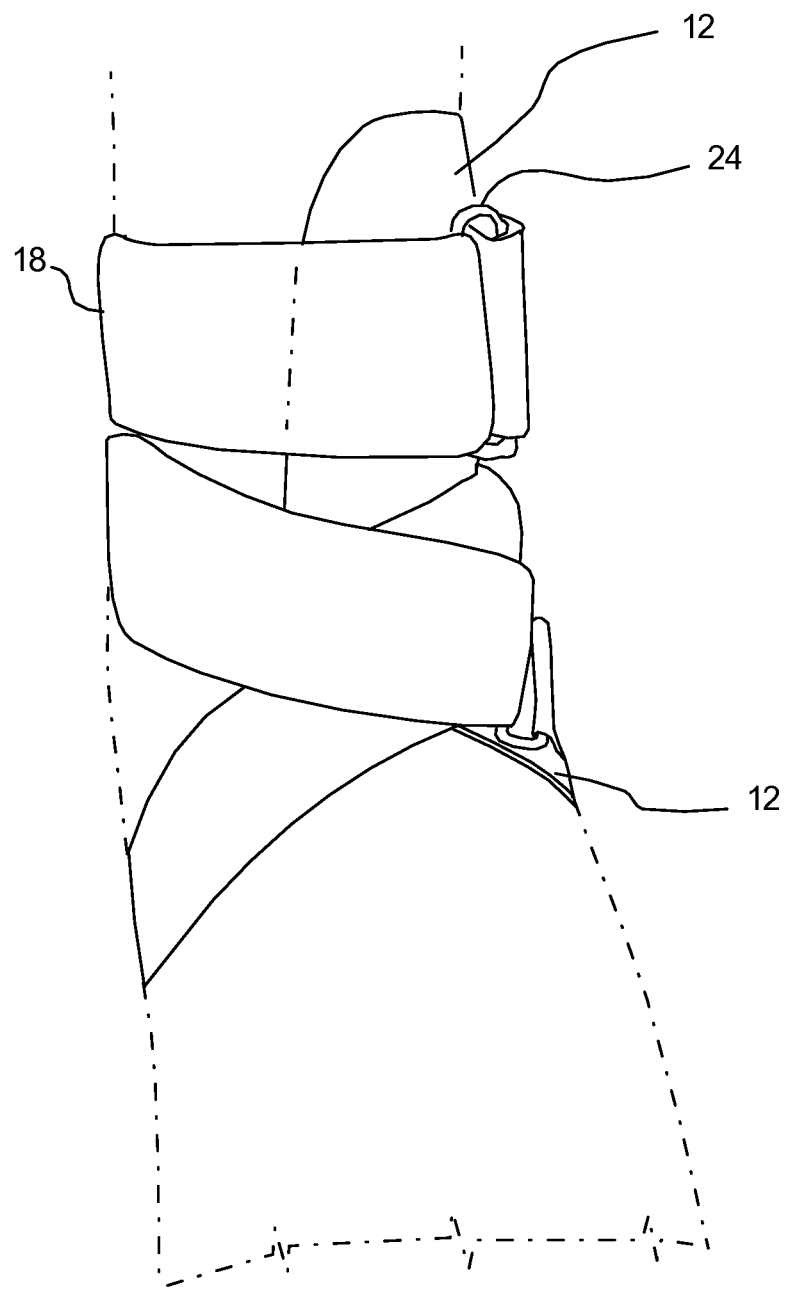
Figure 5:
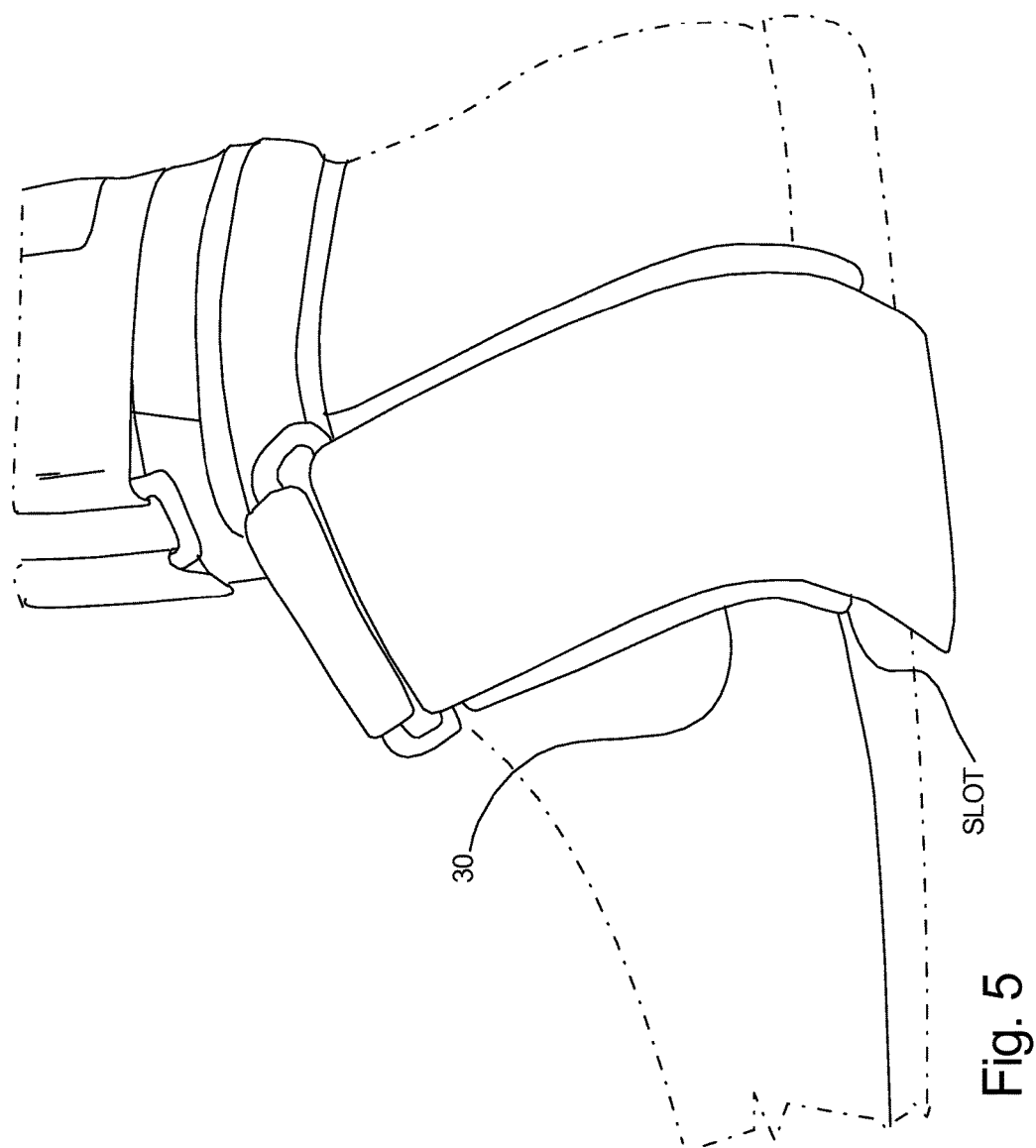
Figure 6:
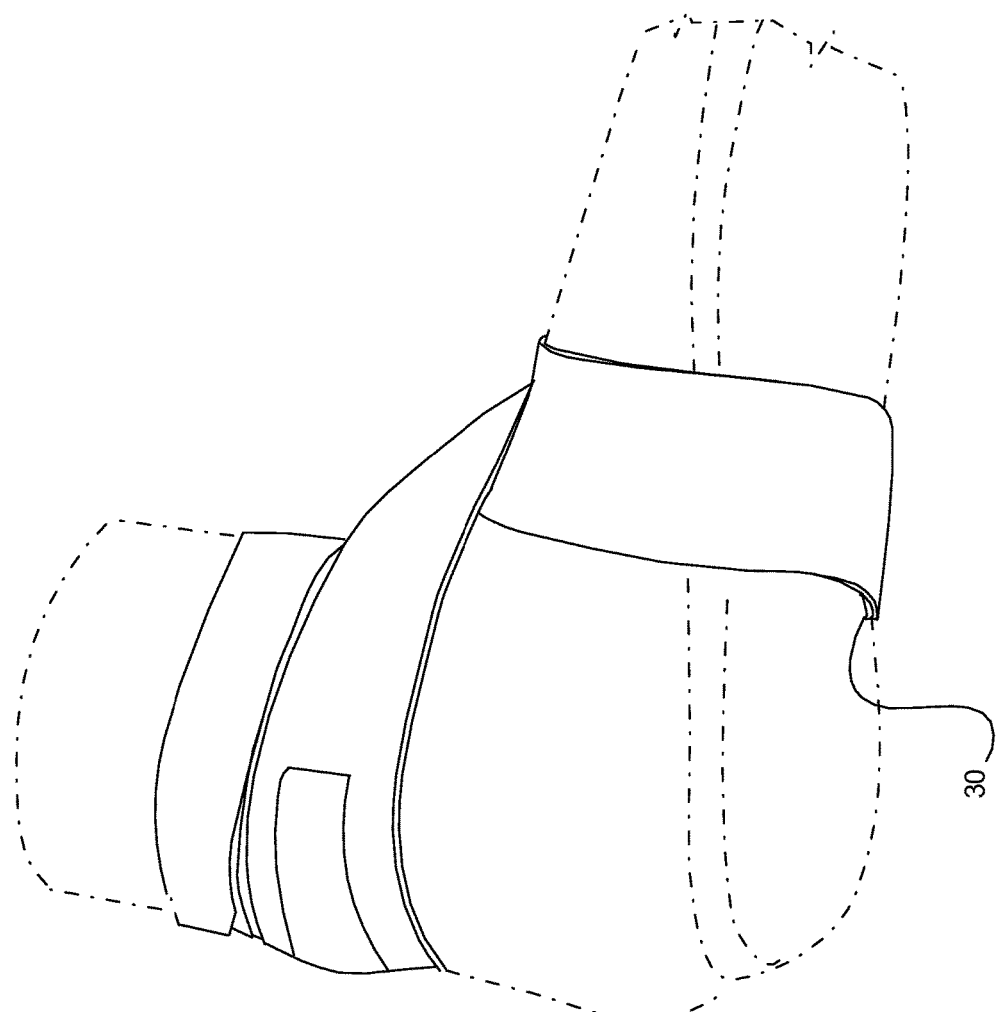
Figure 7:
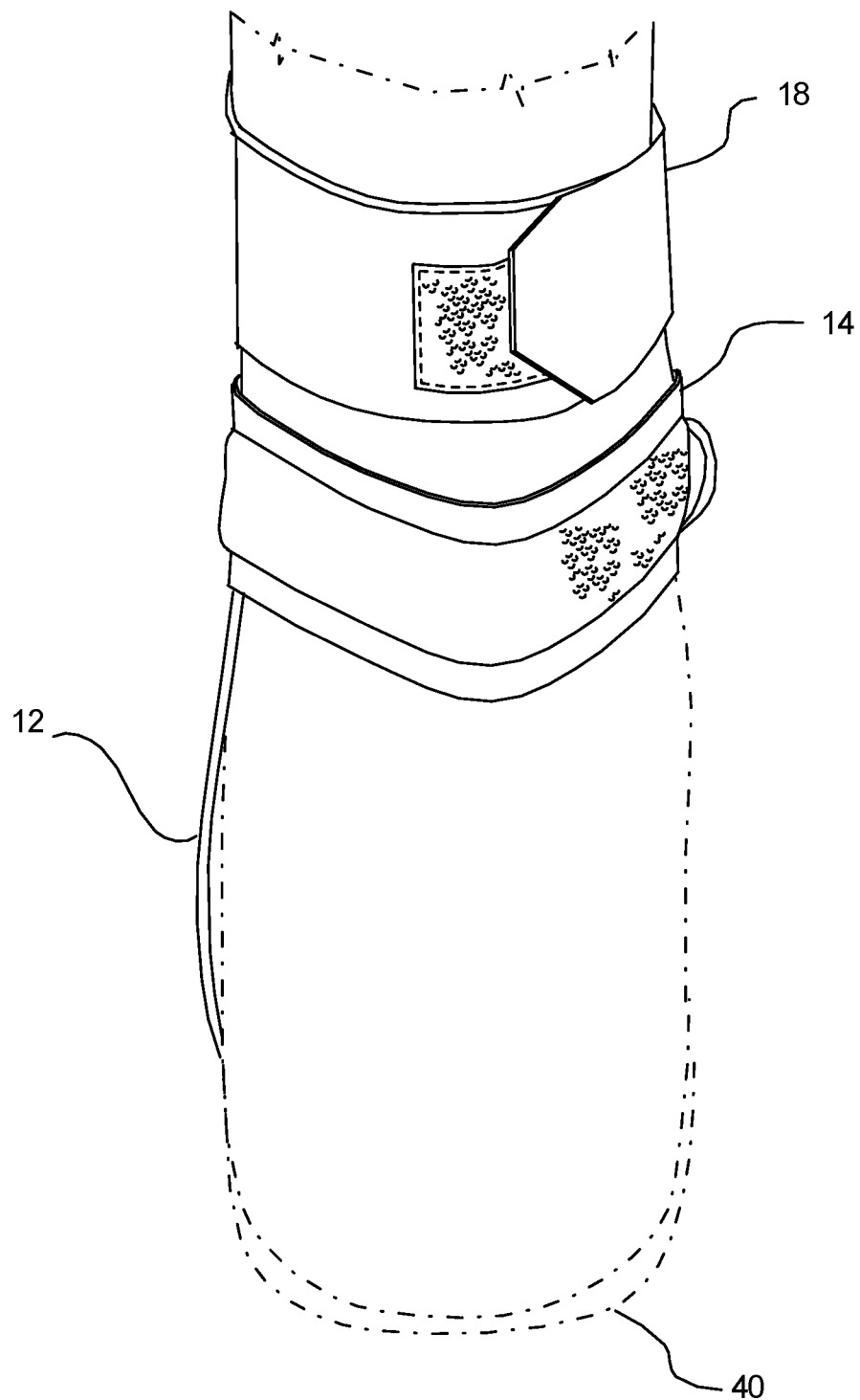

FIG. 3 is another view of the device shown in FIG. 2.
FIG. 4 is another view of the device shown in FIG. 2.
FIG. 5 is another view of the device shown in FIG. 2.
FIG. 6 is another view of the device shown in FIG. 2.
FIG. 7 is another view of the device shown in FIG. 2.

DETAILED DESCRIPTION

Figure 1:
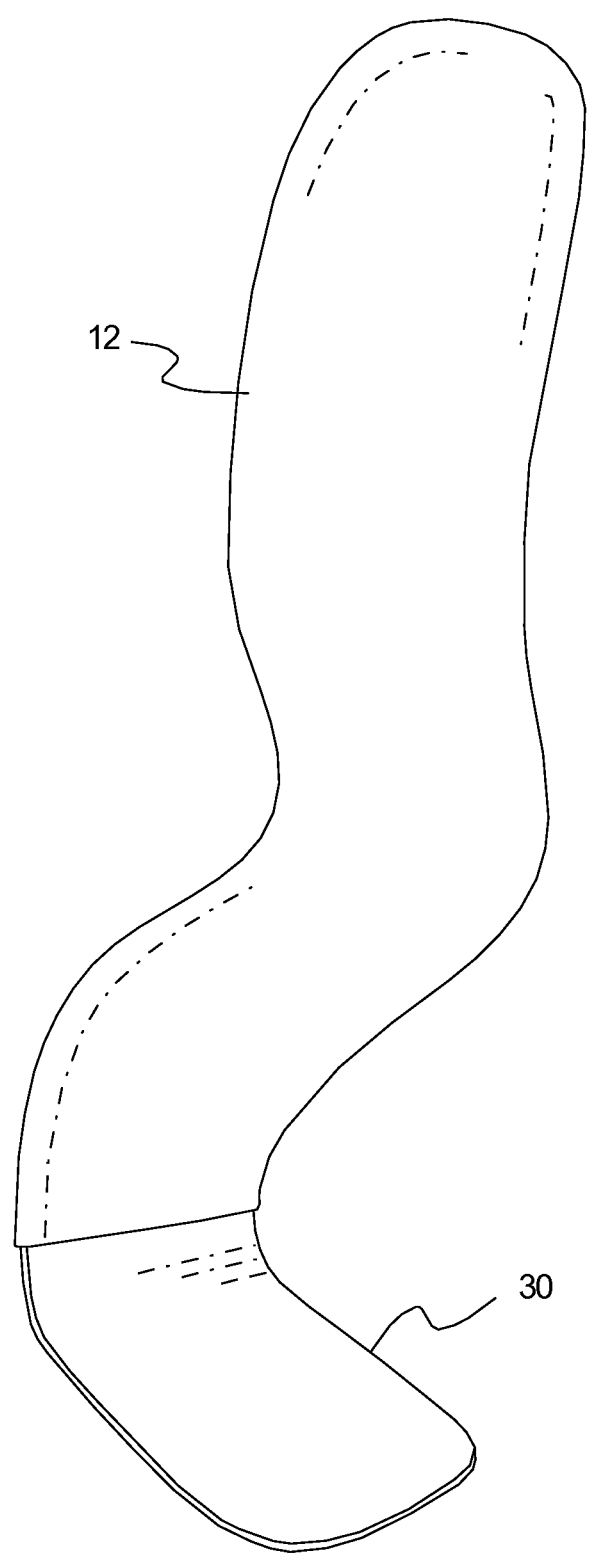
FIG. 1A is a side view of a preferred example of a yoke made in accordance with principles disclosed here.
FIG. 1B is a view looking forward at the yoke illustrated in FIG. 1A.
FIG. 1C is a view looking up at the bottom of the yoke illustrated in FIG. 1A.
FIG. 1D is a view looking up at the section that extends below the wearer's arch while using the yoke as illustrated in FIG. 1C, with the cap that covers the stirrup portion of the yoke removed in order to facilitate use of the yoke while wearing a shoe that enclose the foot.

Turning now to FIG. 1 where a preferred embodiment of an ankle support which has been referenced in the enclosed drawings as ankle support 10 for preventing ankle roll injuries to and for supporting injured ankle joints while wearing shoes or sandals. The support includes a generally L-shaped yoke 12 which can then be mounted against the foot and against the leg. The yoke is held against the leg and foot by means of a pair of straps. One strap, a stirrup or under-foot portion and ankle strap 14, extends from the yoke, below the arch of the foot, up over the front of the foot just below the bottom of the tibia (neck of talus), around just above the exterior ankle, around the Achilles tendon (tendo calcaneus), around just above the interior ankle, down across the front of the bottom of the tibia, and attaches to a first adjustment loop 24 that is mounted on the mid portion of the yoke 12.

The other strap of the invention, the lower calf strap 18, is designed to wind around the lower calf area (peroneus brevis) to lend support to the yoke against the leg.

In the enclosed drawings FIG. 1A shows placement of the yoke 12 against the foot.

FIG. 1B is a view looking forward at the yoke 12 illustrated in FIG. 1A. The yoke 12 is made of a semi-rigid, flexible material, similar to or the same as the material used in the ankle support shown in my U.S. Pat. No. 6,447,469. The embodiment illustrated in FIG. 1B shows the disclosed invention with the use of a removable cap 28, which is preferably made of pliable rubber material. The removable cap 28 is used over the stirrup portion 30 of the yoke 12. It is preferred that the shin portion 31 of the disclosed invention include a pliable rubber shin section cover 32. The shin section cover 32 and the removable cap 28 will include a groove 34 that will accept the mating shin portion 31 of the yoke 12 and a groove 35 for accepting the mating stirrup portion 30 of the yoke. The provision of distinct shin section cover 32 and removable cap 28 will offer important advantages over known art. Importantly, the disclosed invention will allow the user to change shin section cover 32 and removable cap 28 to vary the stiffness of the rubber used in the shin section cover 32 and removable cap 28, or the thickness of either of these components.

The ability to vary the composition and geometry of the shin section cover 32 and/or the removable cap 28 will allow the user to tailor the device to the type of footwear to be worn, and to accommodate variations in individual anatomical differences. For instance, a person with past injuries to the shin may choose to use a very soft foam rubber shin section cover 32.

Additionally, a person who wishes to wear sneakers with the disclosed invention may choose to remove the removable cap 28 while wearing sneakers, and use the removable cap 28 when wearing sandals. Also, since the disclose yoke 12 may be used as a first aid device, the removable cap 28 may be a relatively thick removable cap 28 to allow the user to walk while keeping the rest of the foot above ground. A relatively thick removable cap may simply include a deep transverse slot that will also keep the stirrup portion 30, as well as a strap used with the invention, off the ground.

FIG. 1C is a view looking up at the bottom of the yoke illustrated in FIG. 1A.

FIG. 1D is a view looking up at the section that extends below the wearer's arch while using the yoke as illustrated in FIG. 1C, with the cap that covers the stirrup portion of the yoke removed in order to facilitate use of the yoke while wearing a shoe that encloses the foot.

Referring to FIGS. 2 and 3 it will be understood that the removable cap 28 will also facilitate the use of the disclosed invention with shoes or sneakers, and allow the stirrup portion, without the removable cap 28, to extend under a foam shoe insert 40. It is contemplated that the shoe insert 40 may include a slot or recessed area that will accept the stirrup portion 30, and thus minimize any discomfort associated with the fact that the device is being worn in the shoe.

The described invention prevents injury to the ankle area by preventing rolling of the foot under tibia and thus causing damage or hyper extension of the anterior inferior tibiofibular ligament as well as the interosseous talo-calcanean ligament and other ligaments of the exterior portion of the foot by restraining any such movement by means of a cooperation of the stirrup and ankle strap 14 and the midportion 32 of the yoke 12 against leg and directly over the tibia. The lower calf strap 18 supports the yoke 12 against the lower part of the leg to ensure that load transferred to the yoke 12 is reacted against the lower part of the leg or tibia.

It is important to note that while the disclosed invention has been described as being formable from a single sheet of material to form the stirrup and ankle strap 14, it is contemplated that a highly preferred embodiment of the invention will be made with a stirrup and ankle strap 14 that is made in a pre-shaped form by way of an injection mold. Clearly, it is also contemplated that additional stiffening materials, such as fiber reinforcements, such as graphite fiber or the like, may also be incorporated into the stirrup and ankle strap 14.

The cold pack can be manufactured with the hook and loop material on the packaging, or the system can be provided with adhesive-backed sections of hook and loop material that adheres to the smooth, preferably polymer plastic, material, and which cooperates with loop material on the elastic wrap. The mating loop material of the elastic wrap can be sown or otherwise attached to the elastic wrap, or the fabric of the elastic wrap can be woven so as to provide a suitable amount of looped fibers that will cooperate with the hook material adhered to the cold pack. This arrangement allows the user to position the cold pack at the exact location needed. In the disclosed invention the resilient pad will allow hook or loop material to be affixed to one of the surfaces. This will allow the resilient pad to adhere to the skin, and then the cold pack can then be attached to the resilient pad though the use of the hook and loop material on the cold pack, and then the wrap can be placed over the two. Alternatively, the resilient pad can be adhered to the skin, then the wrap can be used over the resilient pad, and then the cold pack adhered to the wrap. The cold pack can then be further secured and pressed against the injured area with the wrap.

It can be appreciated that the above-described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. An ankle support for facilitating use of an ankle joint of a person, the person being afflicted by an ankle roll injury by supporting the injured ankle while wearing shoes or sandals wearing over a person's lower leg and foot as an aid for facilitating mobility to facilitate mobility of the user and the injured ankle joint, the ankle support comprising:
    a yoke made of a semi-rigid, flexible material, the yoke having a shin portion and a generally planar flat stirrup portion, the flat stirrup portion extending away from the shin portion in a horizontal manner when the shin portion is in a vertical position;
    a removable cap that is adapted for extending over the stirrup portion of the yoke, the cap further having a groove for engaging the stirrup portion of the yoke;
    a shin section cover, the shin section cover adapted for extending over the shin portion of the yoke and includes a groove that will accept a mating portion of the yoke, so that the shin section cover can be varied independently of the cap, and so that the ankle support may be worn with the cap engaged over the stirrup portion and between the foot and the stirrup portion, and without the cap while wearing shoes.

2. An ankle support according to claim 1 and further comprising a shoe insert with an upper surface that is adapted to accommodate the person's foot, and a lower surface that is at a distance from the upper surface, the shoe insert having a recessed area that is adapted for accepting the stirrup portion of the yoke, so as to minimize any discomfort associated with the wearing the ankle support while wearing shoes over the shoe insert.

3. An ankle support according to claim 1 wherein said cap is made of a pliable material, and said groove extends into the cap so that the stirrup portion is accepted within the groove, and so that the ankle support and cap may be worn together against the foot and the lower portion of the wearer's leg.

4. An ankle support system for use within a shoe to be worn over a person's lower leg and foot, the ankle support system comprising:
- a yoke made of a semi-rigid, flexible material, the yoke having a shin portion and a flat stirrup portion that is of integral, one piece, construction with the shin portion, the stirrup portion having a top surface that is bounded by a perimetral edge that extends away from the shin portion;
- a removable cap that is adapted for extending over the stirrup portion of the yoke, the cap having a perimetral groove for engaging the stirrup portion of the yoke, and covering the top surface of the stirrup portion;

a shoe insert adapted for use within the shoe, the shoe insert being adapted for accommodating the foot from below the foot, the shoe insert having a concave groove that is adapted for accepting the stirrup portion of the yoke, so that the yoke, the shoe insert and the shoe accommodate the foot and the yoke together within the shoe with the stirrup portion to be secured against the wearer's foot.

\* \* \* \* \*